US012576271B2

(12) United States Patent  (10) Patent No.: US 12,576,271 B2
McKeown  (45) Date of Patent: Mar. 17, 2026

(54) SYSTEMS, DEVICES AND METHODS FOR ANXIETY TREATMENT USING VESTIBULAR NERVE STIMULATION

(71) Applicant: NEUROVALENS,LTD, Portgleone (GB)

(72) Inventor: Jason McKeown, Portglenone (GB)

(73) Assignee: NEUROVALENS LIMITED, Portglenone (GB)

( * ) Notice: Subject to any disclaimer, the term of this patent is extended or adjusted under 35 U.S.C. 154(b) by 315 days.

(21) Appl. No.: 17/207,491

(22) Filed: Mar. 19, 2021

(65) Prior Publication Data

US 2021/0290958 A1      Sep. 23, 2021

Related U.S. Application Data

(60) Provisional application No. 62/992,020, filed on Mar. 19, 2020.

(51) Int. Cl.
*A61N 1/36* (2006.01)
*A61M 21/00* (2006.01)
(Continued)

(52) U.S. Cl.
CPC ......... *A61N 1/36025* (2013.01); *A61M 21/02* (2013.01); *A61N 1/0456* (2013.01); *A61N 1/36034* (2017.08); *A61M 2021/0072* (2013.01)

(58) Field of Classification Search
CPC . A61M 21/02; A61M 2210/06; A61N 1/0456; A61N 1/0526
(Continued)

(56) References Cited

U.S. PATENT DOCUMENTS 4,558,703 A     12/1985  Mark
6,077,237 A      6/2000  Campbell et al.
(Continued)

FOREIGN PATENT DOCUMENTS

CN        101773702 A     7/2010
JP          6653500 B2     2/2020
(Continued)

OTHER PUBLICATIONS

Krystal, A., The Effect of Vestibular Stimulation in a Four-Hour Sleep Phase Advance Model of Transient Insomnia, Journal of Clinical Sleep Medicine, 2010, pp. 315-321, vol. 6.

*Primary Examiner* — Carrie R Dorna
*Assistant Examiner* — Joshua Daryl D Lannu
(74) *Attorney, Agent, or Firm* — Eleanor Musick; Torrey Pines Law Group PC

(57)  ABSTRACT

Methods, systems and devices are provided to stimulate the vestibular system in such a way as to influence the neurological components of the autonomic nervous system and reduce an anxiety level in a subject. A device with one or more electrodes placed over a subject's scalp provides vestibular nerve stimulation (VeNS) to the vestibular nerve, which is then carried into the vestibular nucleus in the brainstem and thereafter transmitted to the neurological components of the autonomic nervous system to reduce a physiological reaction to an anxiety event. The characteristics of the stimulation signal and duration of the treatment are configured to allow the treatment to be delivered before, during or after an anxiety event to potentially prevent or at the very least reduce an anxiety response in the subject.

20 Claims, 11 Drawing Sheets

(51) Int. Cl.
    *A61M 21/02*         (2006.01)
    *A61N 1/04*          (2006.01)

(58) Field of Classification Search
    USPC ........................................................... 600/26
    See application file for complete search history.

(56)            References Cited

U.S. PATENT DOCUMENTS

| | | | |
|---|---|---|---|
| 6,219,578 B1 | 4/2001 | Collins et al. | |
| 6,656,137 B1* | 12/2003 | Tyldsley | A61M 21/00 |
| | | | 472/60 |
| 6,748,275 B2 | 6/2004 | Lattner et al. | |
| 7,856,275 B1 | 12/2010 | Paul et al. | |
| 8,041,429 B2 | 10/2011 | Kirby | |
| 8,262,717 B2 | 9/2012 | Rogers et al. | |
| 8,718,796 B2 | 5/2014 | Cevette et al. | |
| 9,132,271 B2 | 9/2015 | Kolen et al. | |
| 9,731,125 B2 | 8/2017 | McGeoch et al. | |
| 10,569,084 B2 | 2/2020 | McGeoch et al. | |
| 10,675,465 B2 | 6/2020 | McGeoch et al. | |
| 2002/0026219 A1 | 2/2002 | Collins et al. | |
| 2008/0275293 A1 | 11/2008 | Lattner et al. | |
| 2008/0288016 A1 | 11/2008 | Amurthur et al. | |
| 2008/0308112 A1 | 12/2008 | Aarts | |

| | | | |
|---|---|---|---|
| 2009/0082831 A1 | 3/2009 | Paul et al. | |
| 2009/0182399 A1 | 7/2009 | Sylvestre | |
| 2010/0112533 A1 | 5/2010 | Chan et al. | |
| 2010/0112535 A1 | 5/2010 | Chan et al. | |
| 2010/0113150 A1 | 5/2010 | Chan et al. | |
| 2010/0114187 A1 | 5/2010 | Chan et al. | |
| 2010/0114188 A1 | 5/2010 | Chan et al. | |
| 2010/0114255 A1 | 5/2010 | Chan et al. | |
| 2010/0114256 A1 | 5/2010 | Chan et al. | |
| 2010/0211142 A1 | 8/2010 | Rogers et al. | |
| 2011/0172726 A1 | 7/2011 | Snyman et al. | |
| 2011/0313498 A1 | 12/2011 | Rogers et al. | |
| 2012/0289869 A1* | 11/2012 | Tyler | A61N 7/00 |
| | | | 601/2 |
| 2012/0316625 A1 | 12/2012 | Smith et al. | |
| 2013/0296987 A1 | 11/2013 | Rogers et al. | |
| 2013/0317515 A1 | 11/2013 | Kuroda et al. | |
| 2017/0197081 A1* | 7/2017 | Charlesworth | A61N 1/36034 |
| 2017/0304616 A1* | 10/2017 | McGeoch | A61N 1/0456 |
| 2018/0193641 A1* | 7/2018 | Black | A61N 1/36028 |
| 2020/0009383 A1* | 1/2020 | Waclawik | A61N 1/0456 |

FOREIGN PATENT DOCUMENTS

| | | | |
|---|---|---|---|
| WO | 2009039294 A1 | 3/2009 | |
| WO | 2011161562 A1 | 12/2011 | |

* cited by examiner

Waveform output from microcontroller

Voltage output to electrode pads

WIRELESS SYNC

Fingerprint Recognition
Status Indicator
On / Off Button

Stimulation Control

Wireless Charging

Audio Output
Ear Bud

Stimulation Pads

Wireless Charging

SYSTEMS, DEVICES AND METHODS FOR ANXIETY TREATMENT USING VESTIBULAR NERVE STIMULATION

RELATED APPLICATIONS

This application claims the priority of U.S. Provisional Application No. 62/992,020, filed Mar. 19, 2020, which is incorporated herein by reference in its entirety.

BACKGROUND

Field of the Invention

Systems, methods and devices provided herein relate to vestibular stimulation, and more specifically to stimulating the vestibular nucleus to treat anxiety.

Related Art

There are many areas within the brain stem that control automatic functions of the body, such as blood pressure, heart rate, kidney function, body fat and sleep. Additionally, the brain also regulates stress and behavior through physiological reactions that are often complex and not yet fully understood. Anxiety is one of these stress-related mental and physiological responses that begins in the brain and cascades throughout the body into various physiological changes. As with many brain functions, sleep is a complex process that is influenced by different physiological and neurological factors. Key areas of the brain thought to influence anxiety include the hypothalamus, the suprachiasmatic nucleus (SCN) and the intergeniculate leaflet (IGL).

Although anxiety can be a normal, healthy response to certain types of external stress, chronic or uncontrolled anxiety can form the basis for mental and physiological disorders which may lead to continuing mental and physical health issues. Thus, continuing efforts are being made to understand the cause of anxiety, the physiological pathways and the mechanisms which may be utilized to reduce or eliminate anxiety.

The vestibular system may be one pathway to regulating anxiety. The vestibular system is a major contributor to our sense of balance and spatial orientation, and consists in each inner ear of three semicircular canals (which detect rotational movement) and the two otolith organs, termed the utricle and saccule, which detect linear acceleration and gravity (Khan & Chang, 2013). They are called otolith organs as they are fluid filled sacs containing numerous free moving calcium carbonate crystals-called otoliths-which move under the influence of gravity or linear acceleration to act upon receptor cells to alter vestibular afferent nerve activity.

One pathway to regulating anxiety may be through the vestibular system. The vestibular nuclei (in particular, the medial vestibular nucleus or "MVe") are located in the pons and medulla and receive input via the vestibular nerve from the vestibular system. The MVe are thought to project (both directly and indirectly via the parieto-insular vestibular cortex (PIVC)) to the brainstem homeostatic sites of the parabrachial nucleus (PB) and the peri-aqueductal gray (PAG) (see Chapter 1 and Chapter 3, Section 8 in doctoral thesis by McGeoch, 2010). The PB seems to act to maintain homeostasis—i.e., a stable internal physiological milieu—by integrating this vestibular input with sympathetic input (via lamina 1 spino- and trigemino-thalamic tract fibers) and parasympathetic input (via the nucleus of the solitary tract)

(Balaban and Yates, 2004; Craig, 2007; Craig, 2009; McGeoch et al., 2008, 2009; McGeoch, 2010).

It is thought that the PB then acts to maintain homeostasis by means of behavioral, neuroendocrine, and autonomic nervous system efferent (i.e., both sympathetic and parasympathetic) responses (Balaban and Yates, 2004; McGeoch, 2010). Anatomically the PB projects to the insula and anterior cingulate, amygdala and hypothalamus. The insula and anterior cingulate are areas of cerebral cortex implicated in emotional affect and motivation, and hence behavior (Craig, 2009). The hypothalamus plays a vital role in coordinating the neuroendocrine system (Balaban and Yates, 2004; Fuller et al., 2004; Craig, 2007). The amygdala (together again with the hypothalamus and insula) is similarly known to be important in autonomic nervous system control. The PB also outputs to the PAG and basal forebrain, which are also involved in homeostasis (Balaban and Yates, 2004).

Vestibular nerve stimulation ("VeNS") activates all five components of the vestibular apparatus simultaneously using an electrical current (Fitzpatrick & Day, 2004; St. George & Fitzpatrick, 2011), and offers the practical option of being produced commercially for home use without expert supervision. VeNS involves stimulating the vestibular system through the transcutaneous application of a small electric current (usually between 0.1 to 3 milliamps (mA)) via two electrodes. The electrodes can be applied to a variety of locations around the head, but typically one is applied to the skin over each mastoid process, i.e., behind each ear. Some authors term this a "binaural application." If a cathode and an anode are used with one placed over each mastoid, which is the most common iteration, then this is termed a bipolar binaural application of VeNS. The current can be delivered in a variety of ways, including a constant state, in square waves, a sinusoidal (alternating current) pattern and as a pulse train (Petersen et al., 1994; Carter & Ray, 2007; Fitzpatrick & Day, 2004; St. George & Fitzpatrick, 2011).

There have been limited efforts to treat anxiety using vestibular stimulation, and none have produced any definitive effects or determined useful treatment options. Therefore, there is a need for further development of methods and devices to more effectively and efficiently provide vestibular stimulation to treat anxiety and other stress-related disorders.

SUMMARY

Embodiments described herein provide for systems, devices and methods for utilizing vestibular stimulation to treat anxiety by influencing key areas of the brain and autonomic nervous system responsible for regulating the biochemicals related to anxiety and stress. Stimulation can be delivered for a period of time prior to, during or immediately after an anxiety-causing event using customized signal shapes and durations delivered to the vestibular nerves via one or more head-mounted portable electronic devices. The stimulation essentially tells the brain that an anxiety event does not exist, providing an effective method for treating anxiety.

In one embodiment, a method of reducing anxiety in a human subject through delivery of vestibular nerve stimulation (VeNS) comprises: positioning at least one electrode into electrical contact with the human subject and proximate to a location of the subject's vestibular system; and delivering VeNS to the human subject from a current source connected with the at least one electrode.

In another embodiment, a device for reducing anxiety in a human subject comprises: electrodes disposed in electrical contact with the subject's scalp at a location corresponding to the subject's vestibular system; and a current source in electrical communication with the electrodes for delivering vestibular nerve stimulation (VeNS) to the subject.

In a further embodiment, a method of treating anxiety with vestibular nerve stimulation comprises: positioning at least one electrode into electrical contact with the human subject and proximate to a location of the subject's vestibular system; and delivering VeNS to the human subject from a current source connected with the at least one electrode, wherein the VeNS is delivered for approximately 30 to approximately 60 minutes before, during or after an anxiety event.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for stimulation of the vestibular system in such a way as to reduce the physiological reactions of the autonomic nervous system and reduce anxiety in a subject. For example, one method disclosed herein allows for a device with one or more electrodes placed over a subject's scalp to deliver vestibular nerve stimulation (VeNS) to the vestibular nerve, which is then carried into the vestibular nucleus in the brainstem and thereafter transmitted to the neurological components of the autonomic nervous system to affect areas which trigger an anxiety response, allowing the body reduce or prevent an anxiety response. The characteristics of the stimulation signal and duration of the treatment are configured to allow the treatment to be delivered before, during or after an anxiety event that would otherwise trigger an anxiety response in the subject.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Vestibular Stimulation Devices

Figure 1:
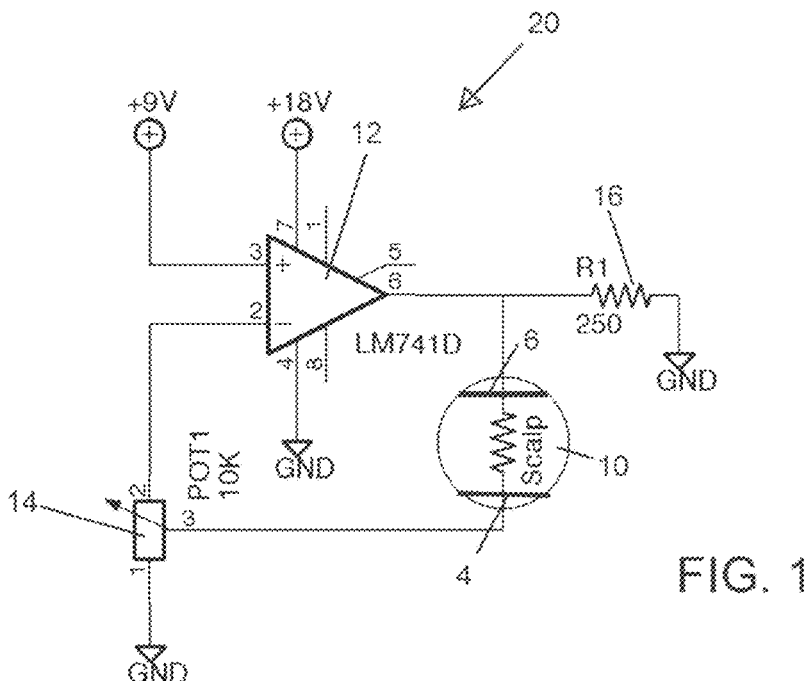
FIG. 1 is a schematic diagram of an exemplary stimulator circuit for a vestibular nerve stimulation (VeNS) device, according to one embodiment of the invention.
Figure 2:
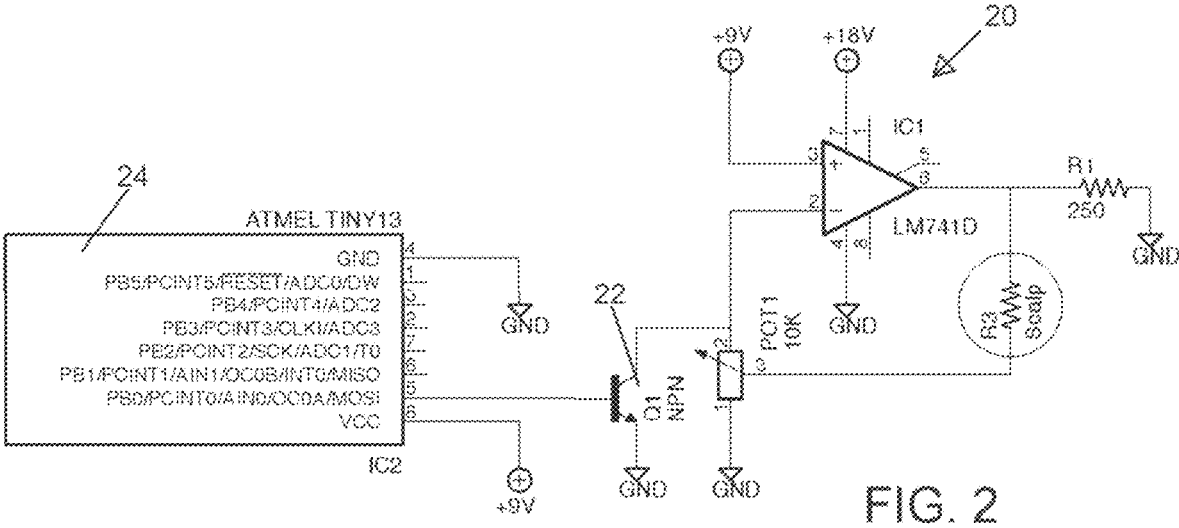
FIG. 2 is a schematic diagram of an alternative embodiment of the stimulator circuit with a gain control component, according to one embodiment of the invention.

FIG. 1 and FIG. 2 illustrate one possible embodiment of the VeNS circuitry that can be employed to carry out the method of the present invention. The device 20 includes a source of time-varying galvanic current that may be software programmable using a microcontroller. In one embodiment, vestibular stimulation may be provided via a head-mounted portable electronic device which is comfortably positioned onto a user's head in an area where stimulation can be delivered to one or both sides of the user's vestibular nerves. Additional illustrations of devices are provided in FIGS. 5 and 10A-10D.

FIG. 1 illustrates the basic components of an embodiment of the stimulation device 20, which includes an operational-amplifier ("op-amp") based constant-current source. A voltage is placed across the scalp 10 through electrodes 4 and 6 and measured by the op-amp 12. In the exemplary embodiment, op-amp 12 may be a general purpose operational amplifier, an example of which is the LM741 series op-amp, which is widely commercially available. Selection of an appropriate operational amplifier will be within the level of skill in the art. If the voltage returning from the scalp 10 to pin 2 (inverting input) of op-amp 12 is different than the reference voltage +9V at pin 3 (non-inverting input), the operational amplifier draws from the +18V input through pin 7 to increase the amount of voltage output at pin 6, thereby increasing the current across the scalp 10 to maintain a constant current level. Load resistor 16 is 250 ohms. Adjustment of potentiometer 14 provides gain control by decreasing the voltage input into op-amp 12 at pin 2, thus controlling the amount of current flowing across the scalp. In the preferred embodiment, the +9V and +18V inputs are provided by one or more batteries (not shown), or a conventional DC converter may be used with appropriate safety provisions.

The schematic in FIG. 2 adds control components to the basic stimulator circuit 20 of FIG. 1. Transistor 22, powered by the pulse-width-modulation (PWM) output (MOSI (master output/slave input, pin 5) of an ATtiny 13 microcontroller 24 (Atmel Corporation, San Jose, CA) or similar device, may be used to control the gain of the stimulator. The PWM causes the transistor to draw more or less of the voltage entering the Op-Amp 12 (pin 2) to ground, thus modulating the amount of current flowing across the scalp.

In a preferred embodiment, the device components and any external interfaces will be enclosed within a housing 30 (shown in FIG. 5) with appropriate user controls 32 for selecting stimulation parameters as appropriate. Note that a knob is shown for illustrative purposes only and that other types of controls, including switches, buttons, pressure bumps, slides, touch screens or other interface devices may be used. Optional design components that may be added to expand the functionality of the device include a memory storage device, such as a memory card or electrically erasable programmable read-only memory (EEPROM), which will allow the time, duration, and intensity of stimulations to be recorded. This can be accomplished by programming the microcontroller 24 to output a logic-level 3.4V pulse (TTL (transistor-transistor logic)) from the remaining digital out (MISO (master input/slave output, pin 6) to a secure digital (SD) memory card, EEPROM, USB flash drive or other data storage device via an appropriate port on the device housing. Additionally, the +18V input may be derived by integrating a charge pump, or DC-DC step-up converter, such as the MAX629 or MAX1683 (not shown). This design feature would have the benefit of reducing the size of the device by producing the necessary +18V input from smaller batteries, which can be disposable or lithium ion rechargeable. Additional features may include wireless communication circuitry, as is known in the art, for programming and/or data collection from a remote computing device, which may include a personal computer, smart phone or tablet computer.

Other functions for implementing VeNS in the present invention may include the ability to pulse the current at precise intervals and durations, in a sinusoidal wave with adjustable amplitude and period, and even switch polarity at precise intervals.

Additional options for facilitating and/or enhancing the administration of VeNS may include a built-in biofeedback capability to adjust the stimulation parameters for optimal effect based on signals generated by sensors that monitor the subject's activity and/or biometric characteristics, such as motion, position, heart rate, etc. For example, real-time heart measured by a heart-rate sensor or monitor can be used as input into the VeNS device, triggering an automatic adjustment of the sinusoidal VeNS frequency to an appropriate, possibly pre-programmed, fraction of the cardiac frequency. Real-time data on the user's motion or position measured by accelerometers may also be used as input to control stimulation, to improve effectiveness and safety. For example, treatment could be terminated if excessive motion or change in the user's position is detected, or the user can be alerted about changes in position that could have adverse effects. The heart rate sensor/monitor and/or accelerometers may be separate devices that communicate with the inventive VeNS device through a wired or wireless connection. Alternatively, sensors may be incorporated directly into the VeNS device to form a wearable "sense-and-treat" system. As new sensors are developed and adapted to mobile computing technologies for "smart", wearable mobile health devices, a "senseand-treat" VeNS device may provide closely tailored stimulation based on a wide array of sensor data input into the device.

Figure 3:
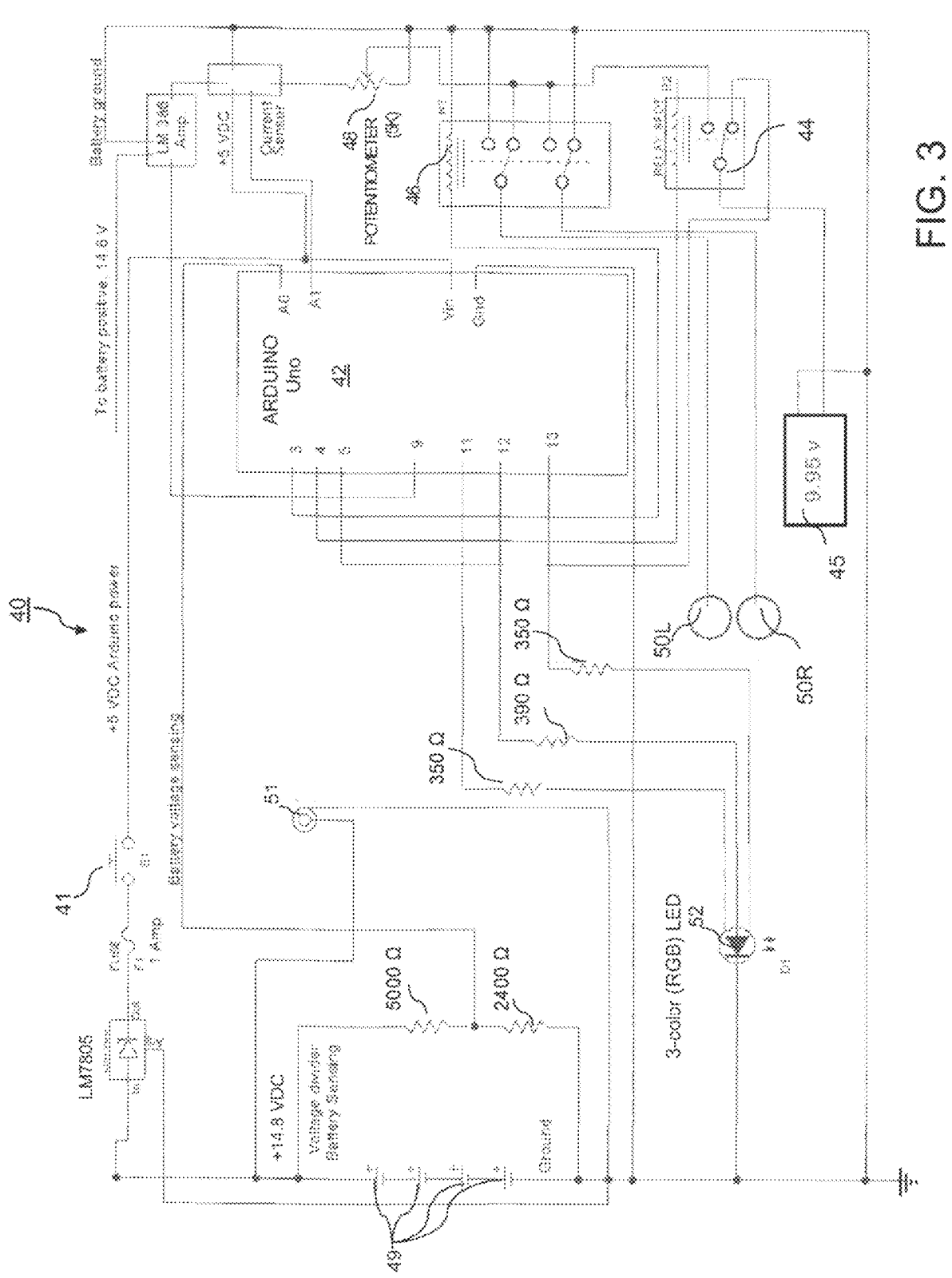
FIG. 3 is a schematic diagram of a second alternative embodiment of the stimulator device, according to one embodiment of the invention.

FIG. 3 schematically illustrates an exemplary prototype of the inventive device 40 implemented using the widely commercially-available ARDUINO® Uno single board microcontroller 42 (Arduino, LLC, Cambridge, MA), which is based on the ATmega328 microcontroller (ATMEL® Corporation, San Jose, CA). Microcontroller 42 includes fourteen digital input/output pins (of which six can be used as pulse width modulation (PWM) outputs), six analog inputs, a 16 MHz ceramic resonator, a USB connection, a power jack, an ICSP header, and a reset button. The +14.8 V DC power to the circuit is provided by batteries 49. For example, four lithium ion batteries, each providing 3.7V (1300 mAh) are used, and are preferably rechargeable via charging port 51.

Figure 4A:
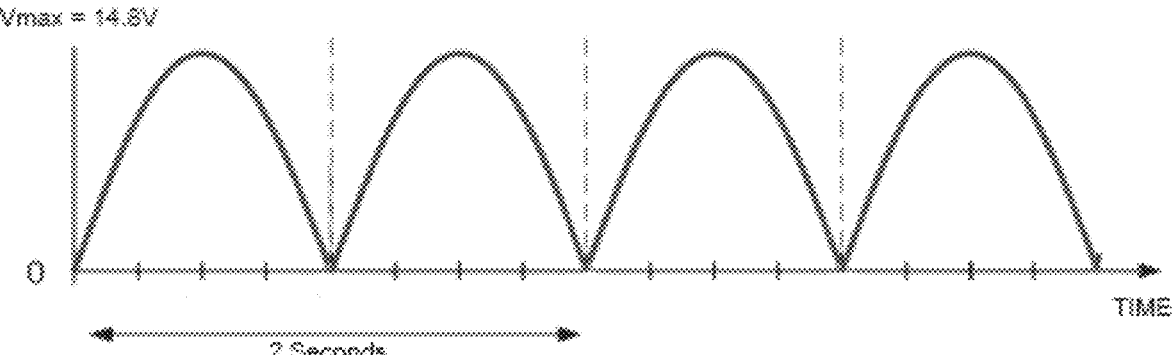
FIGS. 4A and 4B illustrate exemplary wave forms generated by the device, according to one embodiment of the invention.

The PWM allows the output waveform to be accurately controlled. In this case, the waveform takes a repeating half-sine wave pattern in a positive deflection, as shown in FIG. 4A. The frequency has been predefined as 0.25 Hz, but may be set to a different value by manual control or in response to input from a sensor, such as a heart rate sensor (see, e.g., FIG. 5). The user can manually control the amplitude by adjusting the potentiometer 48, allowing a range of 0 to 14.8V to be supplied to the electrodes. This adjustment may be effected by rotating a knob, moving a slide (physically or via a touch screen), or any other known user control mechanism. Alternatively, the potentiometer setting can automatically adjust in response to an input signal from a sensor. Relay 44 communicates the voltage adjustment to a graphical display 45 to provide a read-out of the selected voltage and/or current.

Figure 4B:
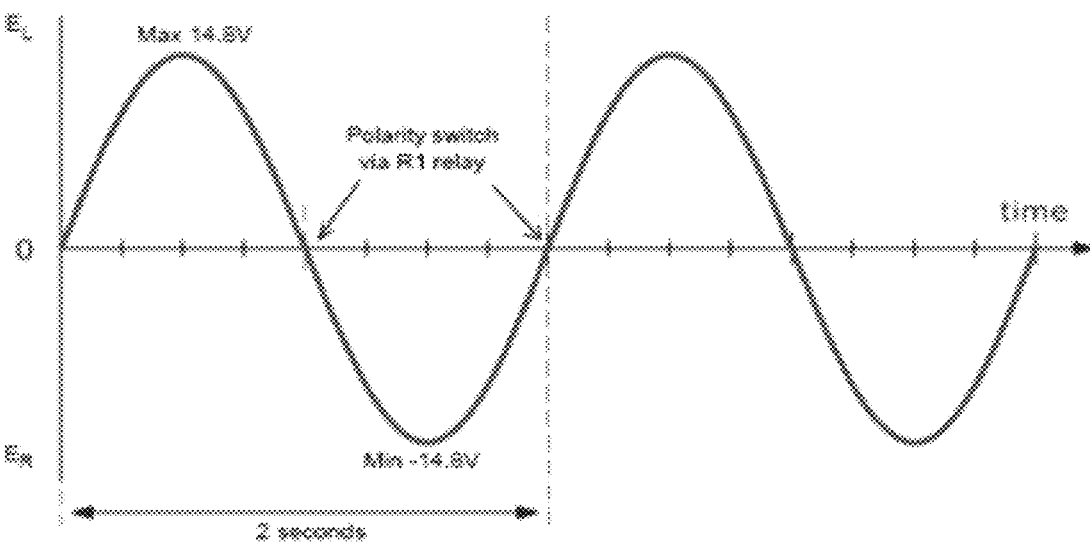

A relay 46 may be employed to effectively reverse the polarity of the current with every second pulse. The effect of this is shown in FIG. 4B, where the sinusoidal pattern changes polarity, thus generating a complete sine waveform to produce alternating periods of stimulation, on the order of 1 second in duration, to the left and right mastoid electrodes 50L and 50R.

The device may optionally include a three color LED 52 that provides a visual display of device conditions, i.e., diagnostic guidance, such as an indication that the device is working correctly or that the battery requires recharging.

Optional design components may include a touch screen configuration that incorporates the potentiometer controls, a digital display of voltage and current, plus other operational parameters and/or usage history. For example, remaining battery charge, previous stimulation statistics and variations in resistance could be displayed. Additional features may include controls for alterations in the waveform such as change of frequency and change of wave type (for example square, pulse or random noise). The ARDUINO® microprocessor platform (or any similar platform) is ideally suited to incorporate feedback control or manual control of frequency, intensity or other stimulation parameters based on an external signal source. For example, the ARDUINO® microprocessor platform, if provided with BLUETOOTH® capability, can be wirelessly controlled by an iPHONE®, ANDROID®, or other smart phone, laptop or personal computer, tablet or mobile device, so that the touchscreen of the mobile device can be used to control and/or display the VeNS stimulation parameters rather than requiring a dedicated screen on the device. The mobile device may also be configured to store and analyze data from previous stimulations, providing trends and statistics about long periods of stimulation, such as over 6 months. Applications of this could allow for programs to monitor and guide users on their progress and goals, highlighting body measurements and changes in weight relative to the periods of stimulation.

An exemplary operational sequence for the embodiment of FIG. 3 for use in treating anxiety may include the following steps:

1. When the push button power switch 41 is activated, the battery (ies) 49 supply 5 volts DC to the microprocessor 42 through a 5 volt regulator and a 1 amp fuse (shown in the figure but not separately labeled.)

2. The LED 52 will flash green three times to indicate the power is "on". If the blue light flashes the battery needs charging. While the voltage is supplied to the electrodes 50L and 50R, the LED 52 will flash red at regular intervals, e.g., 30 seconds to a minute.

3. The microprocessor 42 generates a 0.75 VDC half wave sign wave. The voltage is amplified to 14.8 volts by the amplifier. The sine wave completes one-half cycle in 1 second (i.e., the frequency of the sine wave is 0.25 Hz). The voltage can be varied by the potentiometer 48 from 0 to 14.8 volts.

4. After a half cycle is completed, relay 46 switches polarity of the electrodes 50L, 50R and the microprocessor 42 sends another half cycle. The relay 46 again switches polarity and continues for as long as the unit is "on". This sends a full sine wave of up to +14.8 VDC to the electrodes, with the full voltage swing modulated by the potentiometer 48.

5. A digital display 45 provides a visual indication of the voltage and current delivered to the electrodes 50L, 50R. Depending on the size and complexity of the display, voltage and current values may be displayed simultaneously or alternately for a short duration, e.g., 3 seconds.

Other device options may include user controls to allow the current to be pulsed at precise intervals and durations, a sinusoidal wave to be generated with adjustable amplitude and period, and/or to switch polarity at precise intervals. External control and monitoring via a smart phone or other mobile device as described above may also be included. Further input and processing capability for interfacing and feedback control through external or internal sensors may be included.

Figure 5:
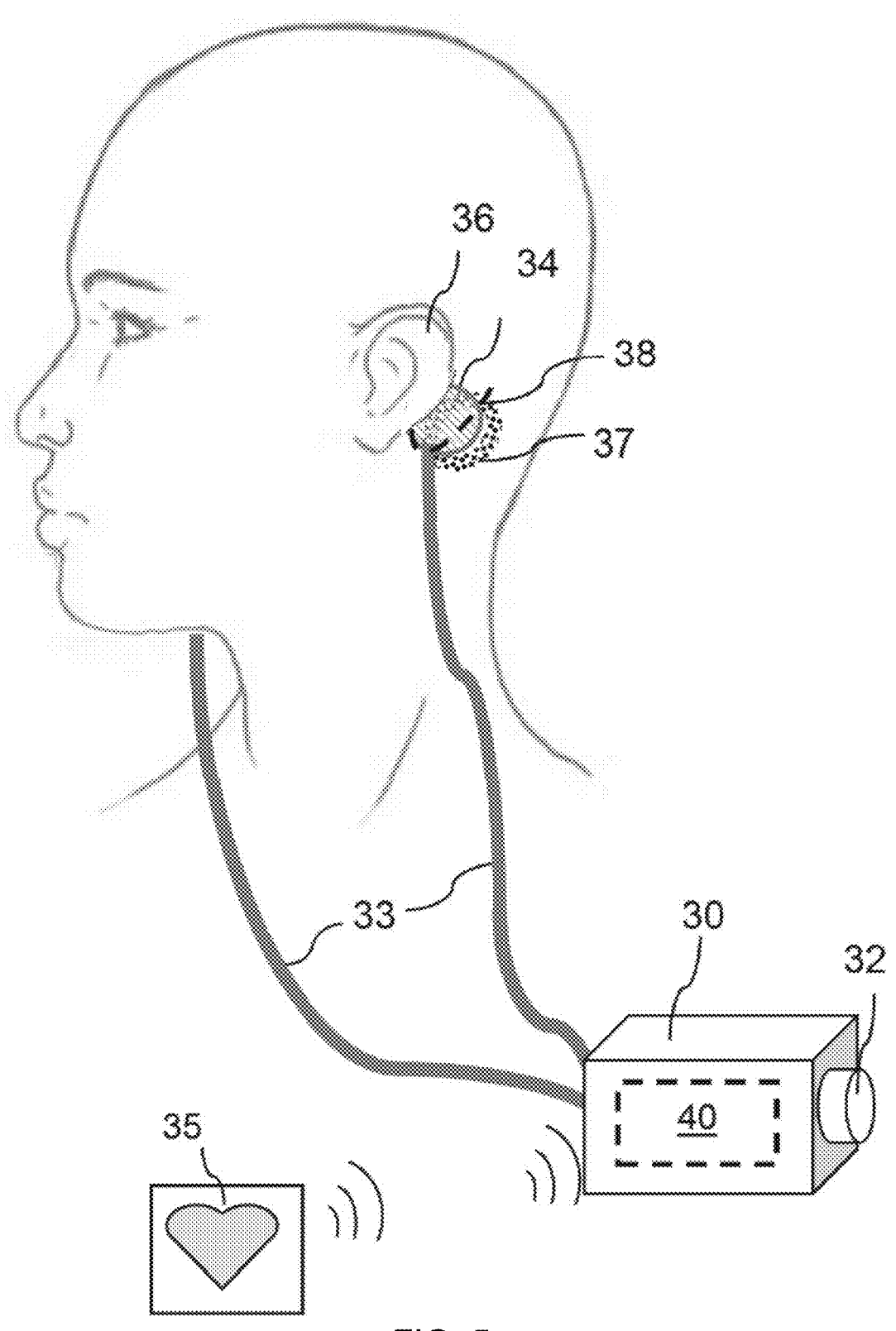
FIG. 5 is a diagram showing an exemplary VeNS electrode placement, according to one embodiment of the invention.

FIG. 5 illustrates an exemplary VeNS electrode 34 positioned on the skin behind the pinna of the left ear 36, and over the left mastoid process, of a subject to be treated. The mastoid process is represented by dashed line 38. The right electrode (not shown) would be placed in the same manner on the skin over the right mastoid process and behind the right pinna. It should be noted that the illustrated placement of the electrodes is provided as an example only. In fact, laterality of the electrode application, e.g., electrodes precisely over both mastoid processes, is not believed to be critical, as long as each electrode is in sufficient proximity to the vestibular system to apply the desired stimulation. The electrodes 34 are connected to stimulation device 40 (inside housing 30) by leads 33. Manual control means, illustrated here as a simple knob 32, may be operated to control the current or other parameters. As described above, alternative control means include a slide, touch screen, buttons or other conventional control devices. External control signals, for example, a signal from a heart rate monitor 35, may be input into the device either wirelessly, as illustrated, or by leads running between the sensor and the device. Electrodes such as the widely commercially available 2×2 inch platinum electrodes used for transcutaneous electrical nerve stimulation (TENS) may be used in order to minimize any possible skin irritation. A conducting gel 37 may be applied between the subject's scalp and the contact surface of the electrodes to enhance conduction and reduce the risk of skin irritation.

The amount of current the subject actually receives depends on the scalp resistance (Iscalp=Velectrodes/Rscalp), which may vary as the user perspires, if the electrode position changes, or if contact with the skin is partially lost. It appears that the current levels quoted in the literature could only be delivered if the scalp resistance was much lower than it actually is. Measurements conducted in conjunction with the development of the inventive method and device indicate that the trans-mastoid resistance is typically between 200 to 500 k-Ohm. Thus, if a VeNS device were actually being used to deliver 1 mA, the voltage would be between 200 to 500V according to Ohm's law. The battery-powered devices that are usually used to administer VeNS are simply not capable of generating such an output. Hence, the existing reports appear to be inaccurate with regard to the actual current being delivered in VeNS.

Prior art designs lack consideration for each subject's unique scalp resistance, and therefore may not deliver an effective current to each patient. In the present invention, this limitation can be overcome by taking into account inter-subject scalp resistance variability as well as compensating for fluctuations in the scalp resistance that may occur throughout the procedure. To compensate for slight and fluctuating changes in scalp resistance during the administration of current, the inventive VeNS device may include an internal feedback loop that continuously compares the desired current against the actual measured current across the scalp and automatically compensates for any differences. If Rscalp increases, the Velectrodes increases to compensate. Conversely, voltage decreases when Rscalp drops. This dynamic feedback compensation loop provides constant current across the scalp for the duration of the procedure regardless of fluctuating changes in electrode-scalp impedance.

Pathways for Anxiety Therapy

Figure 6:
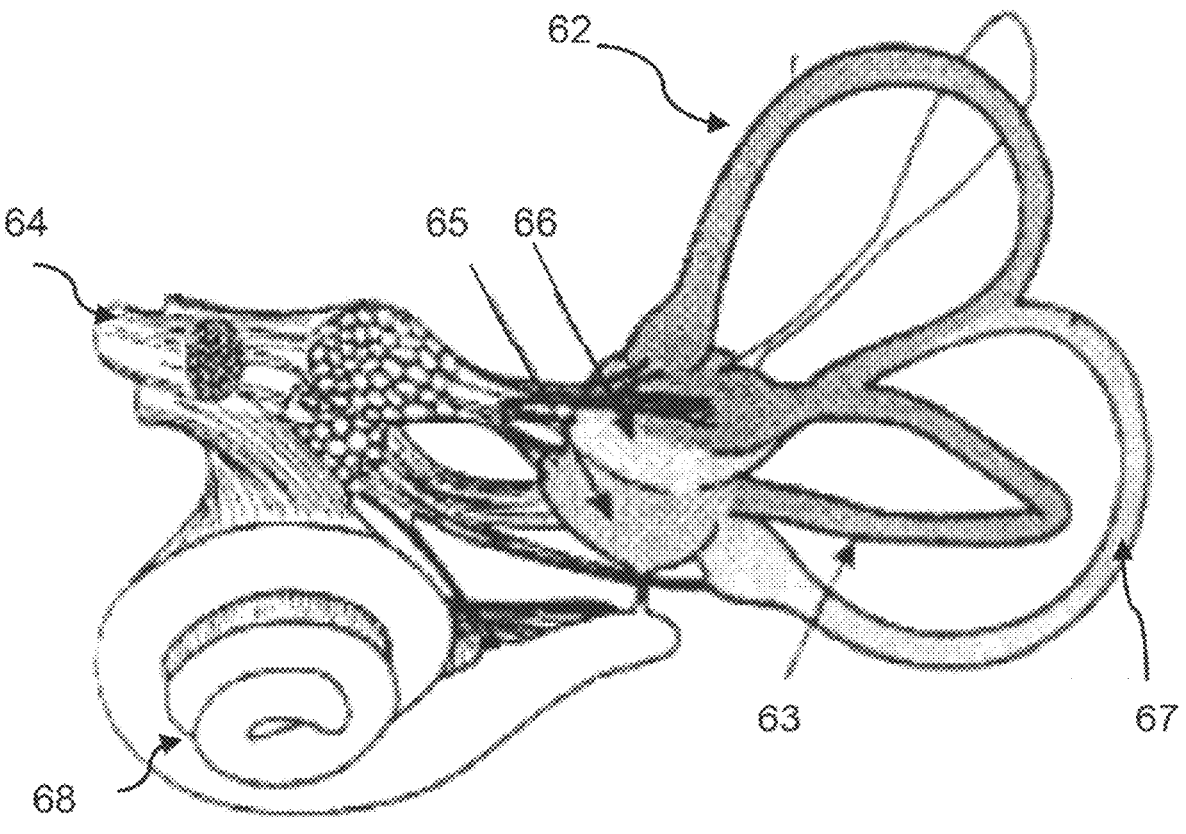
FIG. 6 is a diagram illustrating the vestibular system of the left inner ear.

FIG. 6 illustrates the vestibular system of the left inner ear. The cochlea 68, which is the peripheral organ of hearing, is also shown. It demonstrates: the anterior 62, posterior 67, and horizontal 63 semicircular canals, which transduce rotational movements; and the otolith organs (the utricle 66 and saccule 65), which transduce linear acceleration and gravity. The vestibulocochlear nerve 64 (also known as the eighth cranial nerve) is composed of the cochlear nerve (which carries signals from the cochlea), and the vestibular nerve (which carries signals from the vestibular system).

Figure 7:
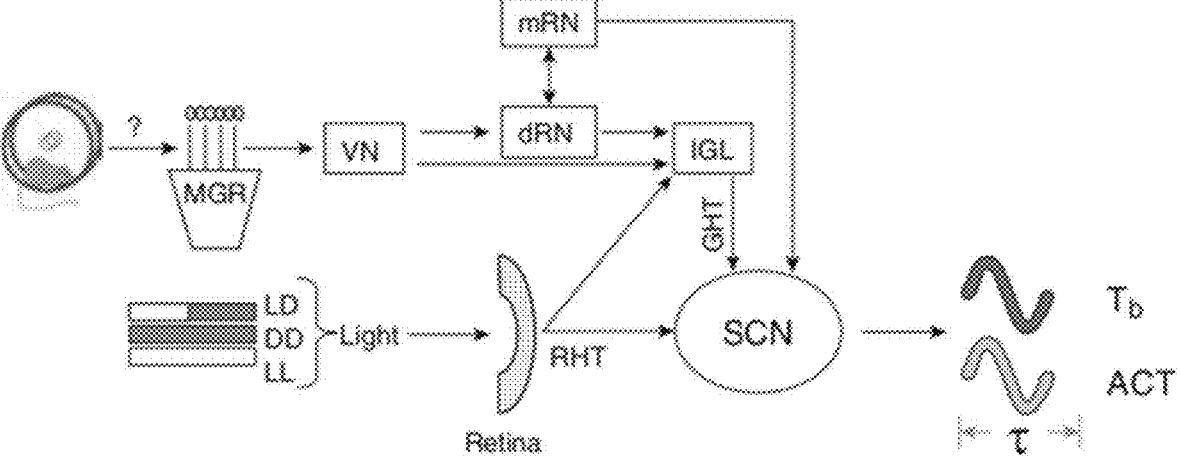
FIG. 7 is a model illustrating anatomical features linking the vestibular and circadian timing systems (CTS)

FIG. 7 is a model outlining potential anatomical features linking the vestibular and circadian timing systems (CTS). Light, the primary synchronizing agent for the CTS, is transmitted to the suprachiasmatic nucleus (SCN) via the retinohypothalamic tract (RHT). Nonphotic stimuli, such as locomotor activity (running wheel), are transmitted to the SCN via the intergeniculate leaflet (IGL) and the geniculohypothalamic tract (GHT). There is also evidence supporting involvement of the serotonergic midbrain raphe (dorsal and medial, dRN and mRN, respectively) in the transmission of activity information to the SCN and IGL. Morphological data also suggest that the vestibular nuclei (VN) may influence the raphe nuclei, particularly the dRN. MGR are the macular gravity receptors, T is the circadian period, and Tb is body temperature.

Vestibular stimulation activates key areas of the brain related to anxiety indirectly by using the vestibular nucleus as a relay, transmitting stimulation of the vestibular system from the vestibular nucleus to the SCN, IGL and hypothalamus. These neurological components influence the physiological response to an anxiety event in the human body, so the application of VeNS essentially re-regulates this physiological response and reduces an anxiety level in the subject.

Treatment Methods

Figure 8:
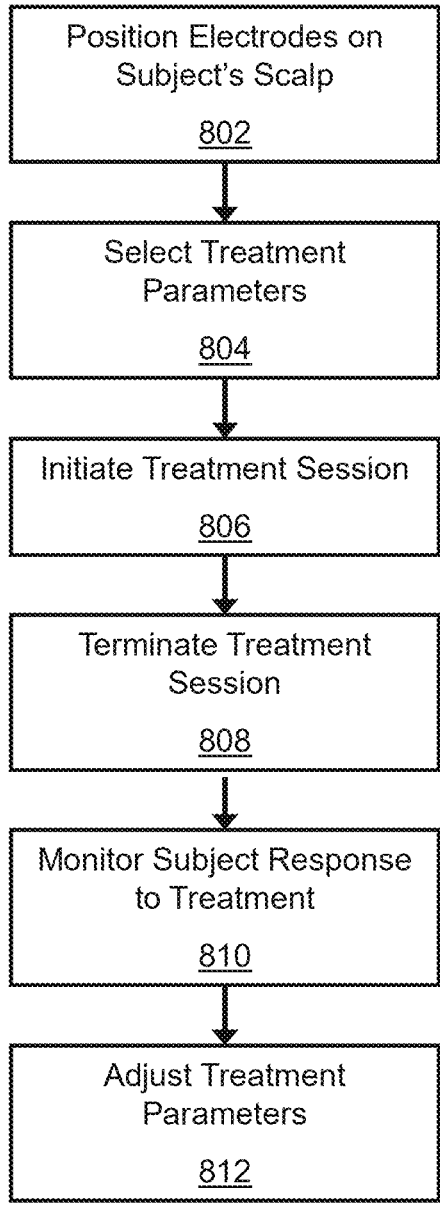
FIG. 8 is a diagram illustrating an exemplary wave form for use in delivering VeNS, according to one embodiment of the invention.

FIG. 8 illustrates one embodiment of a method of utilizing VeNS to reduce anxiety in a human subject. In step 802, one or more electrodes are positioned on the subject's scalp proximate to the location of the vestibular system. The electrodes may be placed on one or both sides of the scalp near the approximate location where stimulation of the vestibular nerve can be achieved. In step 804, the parameters of the VeNS treatment are configured on the VeNS device depending on one or more factors relating to the treatment or the subject, such as the signal shape, pulse, frequency, duration of treatment, time before or after an anxiety event, etc. Once the parameters are selected, the treatment session may be initiated in step 806. In step 808, at the end of the desired treatment duration, the treatment is terminated. In step 810, the subject's response to the treatment may be monitored to determine the effectiveness of the treatment, for example via remote or wearable sensors, the subject's own observations about their anxiety level and duration, and other physiological and psychological factors that may be measured over longer periods of time after multiple treatment sessions. In step 812, the subject's response to the treatment may be utilized to adjust the overall treatment schedule, the parameters of the VeNS or other observed factors that may be influencing the subject's anxiety.

The method of treatment may include delivery of vestibular stimulation at a range of frequencies that are effective at re-regulating autonomic nervous system. In one embodiment, the parameters of a VeNS treatment includes use of a square wave with a frequency of approximately 0.25 Hz and a current range of approximately 0.01 mA-1 mA delivered at an approximately 50 percent duty cycle. The electrodes may be placed bilaterally for delivery of stimulation to both sides of the user's head. The session length of treatment may be approximately 30 minutes to approximately 60 minutes, and the subject may initiate treatment before the expected initiation of an anxiety event.

In another embodiment, the method of treatment may include delivery of vestibular stimulation at varying parameters that may be effective for different types of subjects or with different outcomes relating to the timing of the treatment and the level of anxiety. For example, a range of frequencies from approximately 0.0001 Hz to approximately 10000 Hz, with a range of approximately 0.01 mA to approximately 5 mA, may be utilized with any type of waveform and duty cycle, from square to sinusoidal to pulse. The treatment may be delivered via only one electrode placed on one side of the user's head at the approximate location where stimulation of the vestibular nerve can be made. The user may initiate a treatment at any time prior to, during or after an anxiety event and initiate a treatment session of anywhere from approximately 1 minute to approximately 120 minutes.

In addition to treatments of anxiety and anxiety-related disorders, the aforementioned methods may also be useful in treating other stress or behavior disorders with similar physiological pathways, such as schizophrenia.

Devices for Delivering Anxiety Therapy

A comparable commercially available VeNS device sold under the trademark VESTIBULATOR™ (Good Vibrations Engineering Ltd. of Ontario, Canada) has previously been used in a number of research studies at other institutions. (Barnett-Cowan & Harris, 2009; Trainor et al., 2009.) This device functions with 8 AA batteries, so that the voltage can never exceed 12 V. According to the manufacturer's specifications, the maximum current that this device can deliver is 2.5 mA. The present invention uses a more user-friendly device (e.g., the delivered current can be adjusted using a controller (knob, slide, or similar) on the side of the housing, in comparison to the VESTIBULATOR™, where a similar adjustment can only be carried out by first writing a MATLAB® script and then uploading it remotely, via BLUETOOTH®, in order to reprogram the VESTIBULATOR's™ settings.)

Due to the very small currents used during VeNS, the technique is believed to be safe (Fitzpatrick & Day, 2004; Hanson, 2009). In particular, although electrical current can lead to cardiac arrhythmias, including ventricular fibrillation, the threshold for such an occurrence is in the 75 to 400 mA range, well above the current levels the battery powered VeNS devices can deliver. Furthermore, the electrodes will only be applied to the scalp, such as shown in FIG. 5, and nowhere near the skin over the chest.

Resistive heating can occur with high voltage electrical stimulation of the skin. However, the voltage and current (usually below 1 mA) delivered during VeNS are well below the levels that pose this risk. Nonetheless, skin irritation can occur due to changes in pH. This may be mitigated by using large surface area (approximately 2 inch diameter) platinum electrodes and aloe vera conducting gels.

It may be desirable to monitor the subject's heart rate (HR) to determine the cardiac frequency during VeNS treatment. The cardiac frequency can then be used to alter the frequency of the sinusoidal VeNS so as to maintain a certain ratio between the cardiac frequency and the frequency of the sinusoidal VeNS to avoid interference with baroreceptor activity. For example, a sinusoidal VeNS frequency to cardiac frequency ratio of 0.5 would be appropriate.

During administration of VeNS, one platinum electrode is attached to the skin over one mastoid and the other electrode attached to the skin over the other, as shown in FIG. 5. The electrodes may be coated with conducting gel containing aloe vera. The device is activated to deliver a current of approximately 0.1 mA (given a trans-mastoid resistance of about 500 kOhm) with a sinusoidal waveform at approximately 0.25 Hz. A typical current range for the device would be around 0.001 mA to around 5 mA. The subject may need to remain seated or lying flat throughout the session to avoid mishap due to altered balance during vestibular stimulation, although the device described in FIGS. 10A-10D would not be limited as such. The device is set up to automatically stop after one hour however, the subject may discontinue the treatment sooner if desired. The subject should remain seated until their balance has returned to normal, which should occur within a short period of time after the VeNS device has been turned off.

Figure 9:
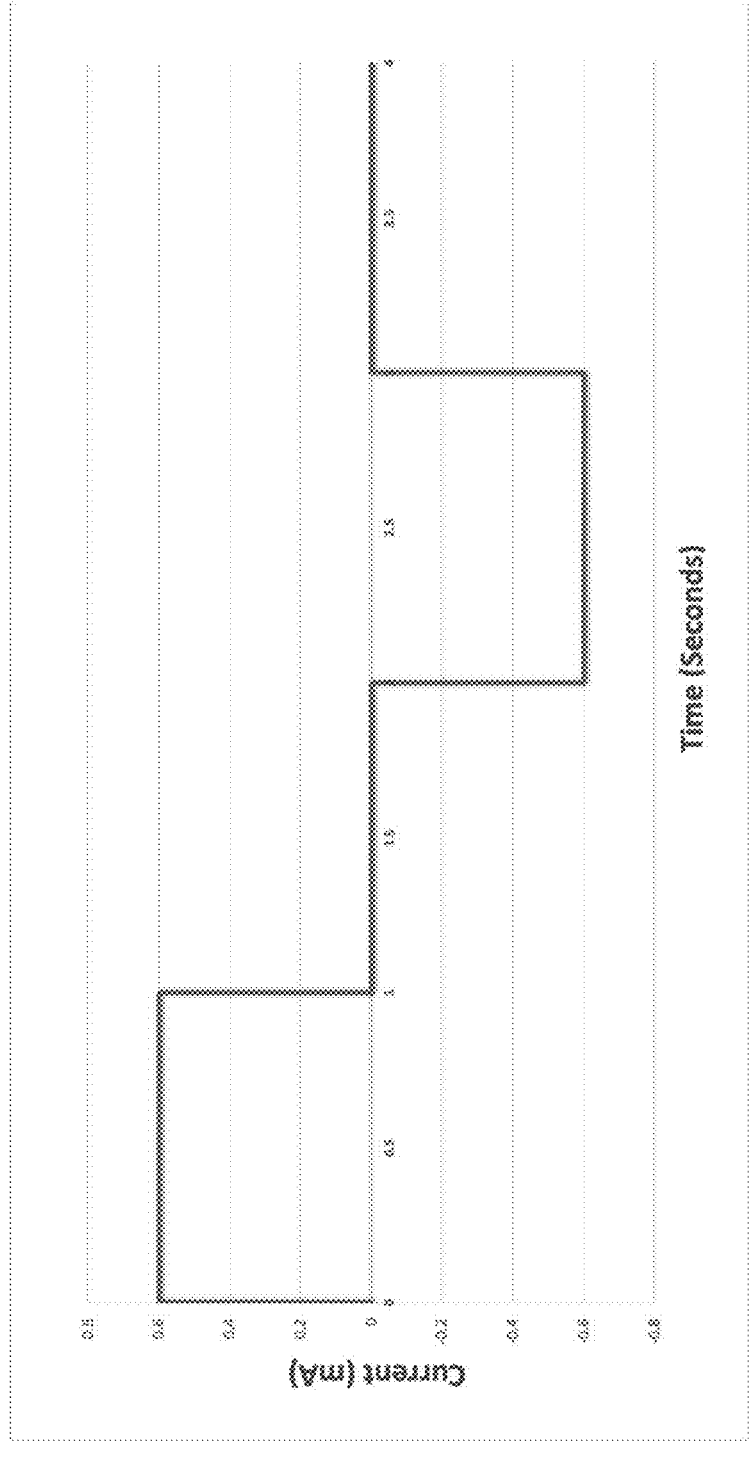
FIG. 9 is a flow diagram illustrating an example method for utilizing VeNS to treat anxiety, according to an embodiment of the invention.

In one embodiment, a VeNS device provided by the company Neurovalens Ltd was used to deliver the stimulation. This device delivers a VeNS current waveform as illustrated in FIG. 9, which consists of an AC square wave at approximately 100 Hz with an approximately 50% duty cycle. The protocol followed was that for the first 30 minutes each subject underwent indirect calorimetry alone in order to establish a baseline. Each subject then underwent a one-hour session of binaural, bipolar VeNS with electrodes placed on the skin over each mastoid as shown in FIG. 5. As stated above an AC square wave at approximately 100 Hz with an approximately 50% duty cycle was delivered, in all subjects with a current of 0.6 mA, although the device used is capable of delivering more.

Figure 10A:
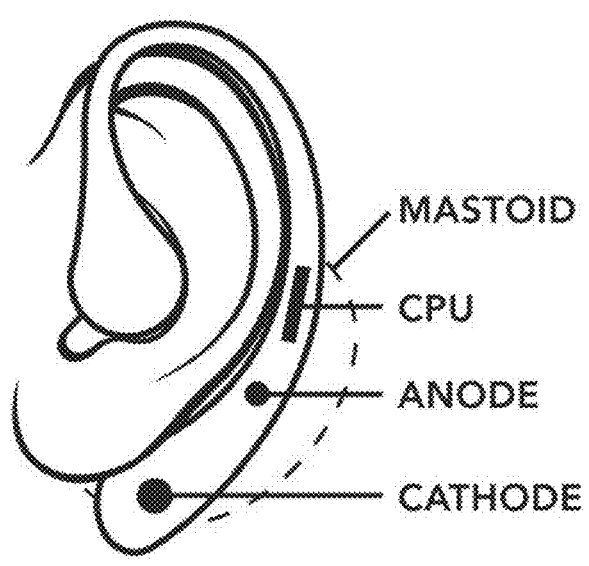
FIG. 10A is an illustration of a vestibular nerve stimulation device positioned around a mastoid process and an ear of a patient for use in treating anxiety, according to one embodiment of the invention.

FIG. 10A illustrates one possible embodiment of a VeNS stimulator which avoids the side-effect of altering a balance of the subject during stimulation by providing simultaneous binaural stimulation from two devices secured on both mastoid processes. Specifically, two stimulators are configured for placement around the subject's left and right ears such that the anode and cathode electrodes are in electrical contact with each mastoid process on the right and left side of the subject's head. The device includes a source of time-varying galvanic current that may be software programmable using a microcontroller (CPU), including a communications interface which allows the VeNS stimulator to communicate with one or more additional stimulators or a master controller in order to synchronize multiple stimulators and coordinate the delivery of VeNS to various locations where the vestibular system may be affected. In one embodiment, vestibular stimulation may be provided via this ear-mounted portable electronic device which is comfortably positioned over a subject's ear in an area where stimulation can be delivered to one or both sides of the user's vestibular nerves.

Figure 10B:
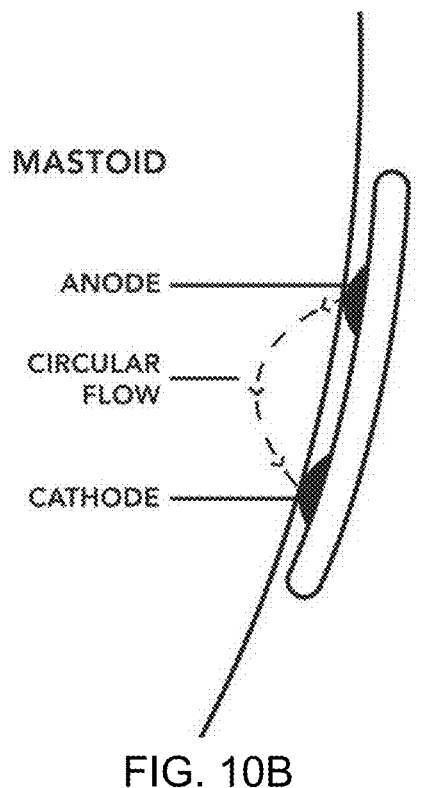
FIG. 10B is an illustration of a circular flow of current between an anode and a cathode provided by the vestibular nerve stimulation device, according to one embodiment of the invention.

FIG. 10B is a side view illustration of the VeNS stimulator which illustrates how the stimulator is a single-sided two pad device with the anode and cathode pads positioned on the same side of the stimulator and adjacent with the mastoid process of the subject. FIG. 10B additionally illustrates how the flow of current in the VeNS stimulator moves from the anode to the cathode across the mastoid process in order to stimulate the vestibular system. While some vestibular stimulation devices place an anode on one stimulation pad on one side of the subject's head and a cathode on a second stimulation pad on the other side of the subject's head in order to deliver the stimulation across the subject's brain, this VeNS stimulator provides both the anode and cathode on a single stimulation pad and thus creates a localized stimulation of the vestibular nerve. This localized stimulation can then be replicated at another location, as will be described immediately below.

Figures 10C, 10D:
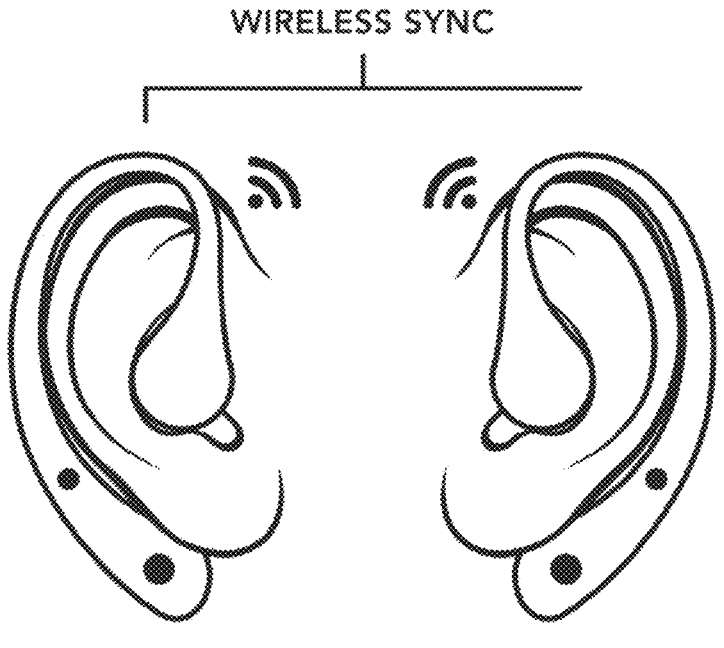
FIG. 10C is an illustration of a wireless communication capability between vestibular nerve stimulation devices positioned on opposing ears of the patient, according to one embodiment of the invention.
FIG. 10D is an illustration of the vestibular nerve stimulation device incorporated into an around-ear headphone, according to one embodiment of the invention.

FIG. 10C illustrates one embodiment of a set of binaural, synchronized VeNS stimulators, with a first stimulator located on a left ear of the subject and a second stimulator located on a right ear of the subject. The two VeNS stimulators may communicate wirelessly in order to synchronize and coordinate the delivery of VeNS to the subject from both locations. In one embodiment, the VeNS stimulators deliver VeNS simultaneously from their respective locations such that the left vestibular nerve and right vestibular nerve receive stimulation at the same time. By delivering the treatment simultaneously from opposing side of the subject's head, the rocking sensation created from delivering treatment on only one side of the subject's head (or from delivering stimulation from an anode on one side of the head to a cathode on the other side of the head) is avoided.

In another embodiment, the portion of the VeNS stimulator which fits within the ear canal may also have a set of pads to provide additional stimulation through the ear canal.

Furthermore, in one embodiment the VeNS stimulator may be incorporated into a portable electronic device such as an around-ear headphone, as illustrated in FIG. 10D. The VeNS stimulator may include an ear bud portion with a speaker which fits into the ear canal. The ear bud portion may also include a power button, LED status indicator and a fingerprint recognition sensor for identity management. A lower portion of the VeNS stimulator may be configured for wireless charging.

The incorporation of the VeNS stimulator into a consumer electronic device such as a pair of headphones provides an opportunity for the subject to receive anxiety treatment in public-including during an anxiety-causing event-without the stigma of a conspicuous-looking medical device. For example, a subject could wear the device during a social event which causes anxiety in the subject in order to alleviate the subject's anxiety during the event. Additionally, the subject could wear the device prior to attending the social event in order to prevent or reduce an anxiety response. And alternatively, if the subject experiences an unanticipated anxiety response from an event, the device can be worn after the anxiety event to reduce the anxiety response in the subject.

Computer-Enabled Embodiment

Figure 11:
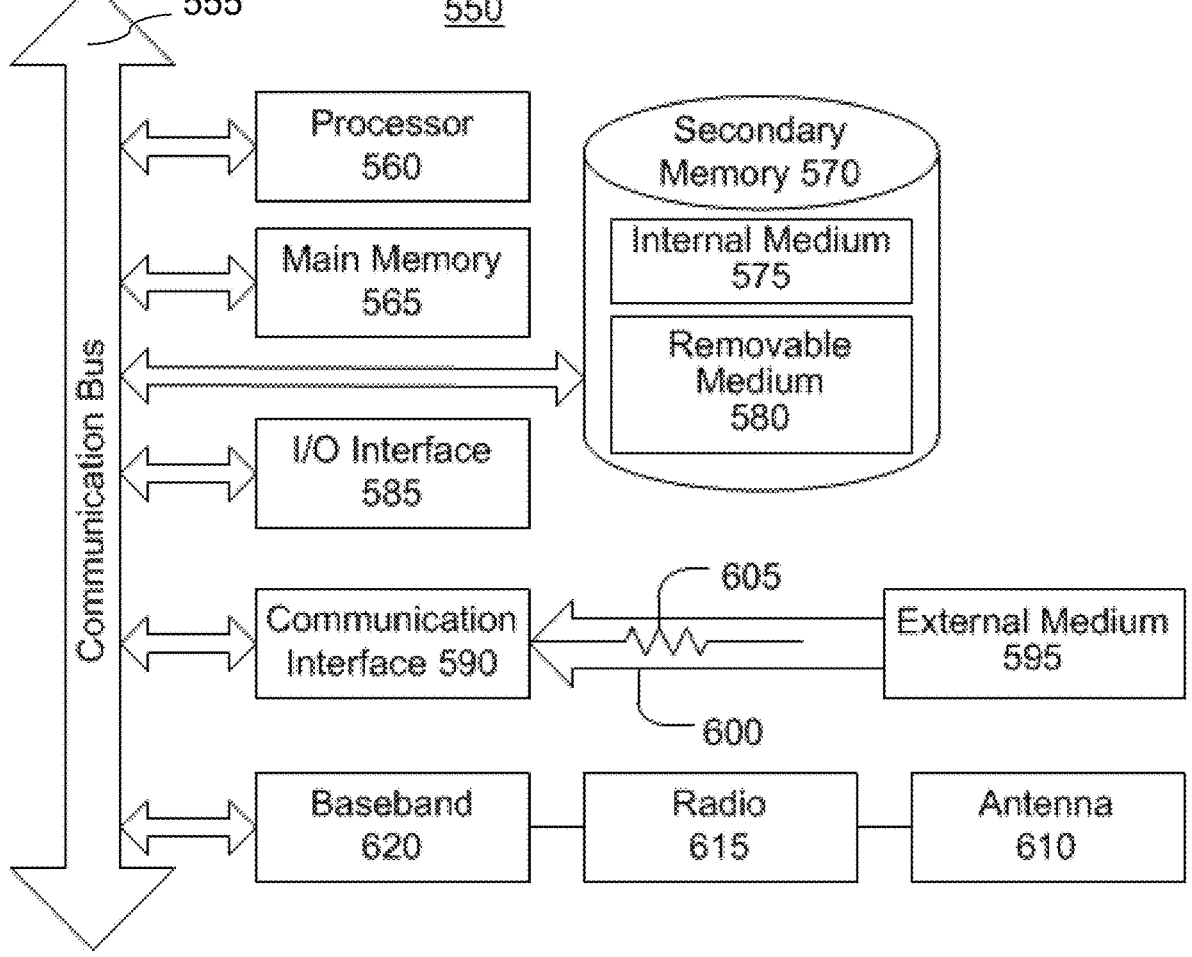
FIG. 11 is a block diagram illustrating an example wired or wireless processor enabled device that may be used in connection with various embodiments described herein.

FIG. 11 is a block diagram illustrating an example wired or wireless system 550 that may be used in connection with various embodiments described herein. For example the system 550 may be used as or in conjunction with a vestibular nerve stimulation device as previously described with respect to FIGS. 1-10. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method of reducing anxiety in a human subject through delivery of vestibular nerve stimulation (VeNS), the method comprising:

positioning at least one electrode into electrical contact with the human subject and proximate to a location of the subject's vestibular system; and delivering VeNS to the human subject from a current source connected with the at least one electrode, the current source configured to deliver an alternating polarity square wave current within a range of 0.01 mA to 1 mA at a frequency of approximately 100 Hz with an approximately 50% duty cycle.

2. The method of claim 1, further comprising delivering VeNS during a social event to alleviate an anxiety response.

3. The method of claim 1, further comprising delivering VeNS for a duration of from 30 to 60 minutes prior to attending a social event.

4. The method of claim 1, where the anxiety is a stress-related disorder.

5. The method of claim 1, wherein positioning at least one electrode comprises applying a conducting gel coating to the at least one electrode.

6. The method of claim 1, further comprising receiving a cardiac frequency measurement from a heart rate monitor and altering the frequency of the alternating polarity current to maintain a ratio between the cardiac frequency and the VeNS frequency.

7. The method of claim 6, wherein the ratio is 0.5.

8. The method of claim 1, wherein the electrodes comprise an anode and a cathode disposed on a single stimulation pad configured to be positioned in electrical contact with the subject's scalp adjacent a mastoid process of the subject, wherein the current within the stimulation pad has a circular flow pattern from the anode to the cathode across the mastoid process.

9. The method of claim 8, wherein the electrodes comprise first and second binaural stimulation pads, wherein positioning comprises disposing the first binaural stimulation pad adjacent a left mastoid process and the second binaural stimulation pad adjacent a right mastoid process, and wherein the current source is synchronized to simultaneously deliver VeNS to each binaural stimulation pad.

10. A device for reducing anxiety in a human subject, the device comprising:

electrodes configured to be disposed in electrical contact with the subject's scalp at a location corresponding to the subject's vestibular system; and a current source in electrical communication with the electrodes for delivering vestibular nerve stimulation (VeNS) to the subject, the current source configured to deliver an alternating polarity current within a range of 0.01 mA to 1 mA with an approximately 50% duty cycle at a VeNS frequency of 100 Hz.

11. The device of claim 10, wherein the device is configured to deliver VeNS for a duration of from 30 to 60 minutes.

12. The device of claim 10, further comprising a device controller in communication with the current source, the controller configured for receiving a cardiac frequency measurement from a heart rate monitor and altering the frequency of the alternating polarity current to maintain a ratio between the cardiac frequency and the VeNS frequency.

13. The device of claim 12, wherein the ratio is 0.5.

14. The device of claim 10, wherein the alternating polarity current is a square wave at 0.6 mA.

15. The device of claim 10, wherein each electrode is coated with a conducting gel containing aloe vera.

16. The device of claim 10, wherein each electrode has a diameter of approximately 2 inches (5.08 cm).

17. The device of claim 10, wherein the electrodes comprise an anode and a cathode disposed on a single stimulation pad configured to be positioned in electrical contact with the subject's scalp adjacent a mastoid process of the subject, wherein delivering VeNS comprises using a circular flow pattern from the anode to the cathode across the mastoid process.

18. The device of claim 17, wherein the electrodes comprise first and second binaural stimulation pads, wherein the first binaural stimulation pad is configured to be disposed adjacent a left mastoid process and the second binaural stimulation pad is configured to be disposed adjacent a right mastoid process, and wherein the current source is synchronized to simultaneously deliver VeNS to each binaural stimulation pad.

19. A method of treating anxiety with vestibular nerve stimulation (VeNS), comprising:

positioning at least one vestibular nerve stimulation (VeNS) stimulator having a cathode pad and an anode pad into electrical contact with a subject's scalp adjacent to the subject's mastoid process proximate to a location of the subject's vestibular system; and delivering VeNS to the human subject from a current source connected with the at least one VeNS stimulator, the current source configured to deliver an alternating polarity current within a range of 0.01 mA to 1 mA and a frequency of 100 Hz with an approximately 50% duty cycle wherein the current flows in a circle from the cathode pad to the anode pad across the subject's mastoid process.

20. The method of claim 19, where the anxiety is a stress-related disorder.

* * * * *